United States Patent [19]

Abe et al.

[11] Patent Number: 4,839,168
[45] Date of Patent: Jun. 13, 1989

[54] HAIR COSMETICS

[75] Inventors: Yoshiaki Abe, Tokyo; Hidetoshi Iwabuchi, Yachiyo, both of Japan

[73] Assignee: Kao Corporation, Tokyo, Japan

[21] Appl. No.: 914,510

[22] Filed: Oct. 2, 1986

Related U.S. Application Data

[63] Continuation of Ser. No. 583,698, Feb. 27, 1984, abandoned.

[30] Foreign Application Priority Data

Feb. 25, 1983 [JP] Japan .................................. 58-30445
Feb. 25, 1983 [JP] Japan .................................. 58-30446

[51] Int. Cl.$^4$ ........................ A61K 7/06; A61K 7/00; A61K 7/09
[52] U.S. Cl. ........................................ 424/74; 424/47; 424/70; 424/71
[58] Field of Search ........................ 424/70, 74, 47, 71

[56] References Cited

U.S. PATENT DOCUMENTS

| | | | |
|---|---|---|---|
| 114,544 | 5/1871 | Fay | 424/195.1 |
| 4,338,214 | 7/1982 | Fischer et al. | 424/70 |
| 4,530,829 | 7/1985 | Abe | 424/70 |

FOREIGN PATENT DOCUMENTS

| | | | |
|---|---|---|---|
| 0057353 | 8/1982 | European Pat. Off. | 424/70 |
| 53466 | 9/1982 | European Pat. Off. | 424/70 |
| 2087991 | 1/1972 | France | 424/70 |
| 2425241 | 1/1980 | France | 424/70 |
| 2437829 | 4/1980 | France | 424/70 |
| 57-179109 | 11/1982 | Japan | 424/70 |
| 59-1408 | 1/1984 | Japan | 424/70 |
| 1568990 | 6/1980 | United Kingdom . | |

OTHER PUBLICATIONS

Keller, *Mysterious Herbs & Roots*, pp. 292–293, (1978).
Lewis, *Medical Botany*, pp. 338–339, 344 (1977).
Chem. Abst. 79:45795k (1973).
Cosvetic Laboratories, Inc. *Body Forum*, vol. 6(5), p. 23 (1981).
Chem. Abst. 76:117517j.

*Primary Examiner*—Douglas W. Robinson
*Assistant Examiner*—R. Kearse
*Attorney, Agent, or Firm*—Oblon, Spivak, McClelland, Maier & Neustadt

[57] ABSTRACT

Hair cosmetic compositions comprise (A) an extract obtained by polar solvent extraction of a plant, preferable ones of which are birch, rosemary and hamamelis, and (B) a polypeptide compound including keratin, keratin derivative, silk and hydrolysate of silk.

Such compositions are made into shampoo, rinse, set lotion, hair spray, etc.

Hair cosmetics according to the invention can impart good hair style retentivity and good touch of feeling.

8 Claims, No Drawings

HAIR COSMETICS

This application is a Continuation of application Ser. No. 583,698, filed Feb. 27, 1984, now abandonded

BACKGROUND OF THE INVENTION (i) Field of the Invention:

This invention relates to hair cosmetic compositions and more particularly, to hair cosmetic compositions of the type which comprise extracts obtained by polar solvent extraction of plants and polypeptide compounds and which can impart, to hair, a suitable degree of set retentivity and good feeling to the touch.

(ii) Description of the Prior Art:

Hair style is one of the most important and charming points from the standpoint of beauty care and a variety of beauty treatments have been made. For instance, several techniques of suitably waving the hair using hair cosmetics are known including so-called permanent treatments by permanent waving techniques and transient treatments using set lotions or hair sprays. By the treatments, the hair is suitably set or dressed. However, the treatments by the permanent waving techniques may sometimes damage the hair considerably to such an extent that the hair cannot refresh. On the other hand, the treatments using set lotions of hair sprays are disadvantageous in that the hair is merely set transiently and thus the once set hair is broken simply by the action of moisture. Hence, both types of treatments are not satisfactory. Moreover, these techniques have the tendency of stiffening the hair and are not also satisfactory in the touch of the hair.

Shampooes are extensively used for the purpose of washing away soiling attached on the hair. However, currently available shampooes also wash away oil necessary for the hair, so that the shampooed hair becomes dry and split-ends or broken hairs are undesirably involved upon brushing. To avoid this, hair rinses or pre-shampooes are used, of which some contain oils or fats, causing the hair sticky.

SUMMARY OF THE INVENTION

In order to obtain hair cosmetic compositions having excellent properties, we have made extensive studies on ingredients of the cosmetics. As a result, it was found that when a combination of a specific type of plant extract and a polypeptide is admixed with hair cosmetic compositions such as shampoo, rinse, set lotion, hair spray and the like, the resulting cosmetic compositions can impart good hair style retentivity and a suitable degree of feeling to the touch with ease in combing.

According to the present invention, there is provided a hair cosmetic which comprises (A) an extract obtained by polar solvent extraction of a plant, and (B) a polypeptide compound.

DETAILED DESCRIPTION OF THE INVENTION AND PREFFERED EMBODIMENTS

The (A) ingredient useful in the present invention is obtained by extraction of plants. Examples of the plant include birch, rosemary, arnica, hamamelis, camomile, sage, St. John's bread, henna, hop, lime, aloe, wild thyme, calendula, horsetail, mountain gentian, nettle, chestnut, avocado, seaweed, milfoil, coltsfoot, marigold, peach, rose, senna, thyme, and white lily. Of these plants, birch, rosemary, hamamelis, camomile, sage, aloe, henna, and St. John's bread are preferable and most preferably mentioned are birch and rosemary.

Preferable sites of these preferable plants for the extraction are, for example, bark of birch, an entire grass part of rosemary, leaves of hamamelis, flower of camomile, leaves of sage, leaves of aloe, leaves of henna, and fruit of St. John's bread.

The plant extract is obtained by extracting flowers, leaves, fruits, roots, stems and the like with solvent at a normal temperture or under heating conditions according to any known extraction technique. The extraction solvents are polar organic solvents including, for example, lower alcohols such as methanol, ethanol and the like, propylene glycol, 1,3-butylene glycol and glycerine, and water. These solvents may be used singly or in combination.

The extracts of birch and rosemary which are the most preferable plants are commercially available. The commercially sold birch extracts include Birch Extract made by Novarom Co., Ltd., Boulene MCF787 by Gattefossé Co., Ltd., Birch Extract by Virmin Co., Ltd., Birch Extract by Nowak Co., Ltd., Extrapone Birch Special by Dragoco Co., Ltd., and the like. Mentioned as rosemary extract are rosemary Extract by Novarom Co. Ltd., Romarin MCF772 by Gattefossé Co. Ltd., Phytelene EG009 by Virmin Co., Ltd., and Rosemary Extract by Nowak Co., Ltd.

When the plant extract is in a liquid form, the ingredient (A) is used in an amount ranging from 0.001 to 10.0 wt %, preferably 0.01 to 1.0 wt % (hereinafter referred to simply as %) of the total compositon, calculated as a residue obtained after distillation of extraction solvent therefrom. The ingredient (A) or plant extract may be directly added to hair cosmetic compositions in the form of liquid extract, or may be added after concentration to a desired level or after complete removal of extraction solvent from the extract.

The ingredient (B) used in the present invention are polypeptide compounds which are, for example, keratin and decomposition derivatives thereof, and silk fibers and hydrolyzate of silk.

Keratin is derived from, for example, animal hairs, human hair, feathers, nails, horns, hooves, scales or the like. These materials may be used in the form of fine powder and are preferably used as a decomposition derivative thereof. Preferable keratin materials are wool, human hair, and feathers.

The decomposition derivatives of keratin materials are hydrolyzates, oxidative decomposition products, and -SH group-modified compounds of reductive decomposition products. The hydrolysis, oxidation and reduction reactions and a subsequent modification reaction may be suitably combined. The hydrolysis techniques include an acid hydrolysis using hydrochloric acid, sulfuric acid, phosphoric acid or the like; and alkali hydrolysis using sodium hydroxide, sodium carbonate of the like; and an enzyme hydrolysis using protease. The oxidation and/or reduction reaction may be effected according to any known method. The disulfide bond is cleft, by the reduction reaction, into a thiol group (-SH). The thiol group can be modified by a known method to give the following groups:

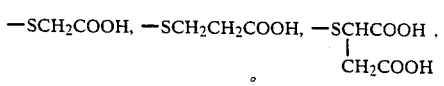

-continued

—SCHCH₂COOH, —SCH₂CHCOOH, —SO₃H, —SSO₃H,
  |                  |
  CH₃               CH₃

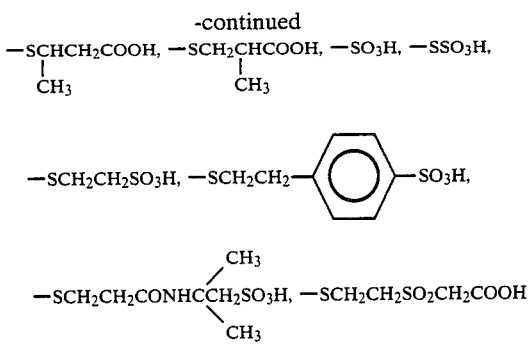

Of these groups, —SCH₂COOH and

—SCHCOOH
  |
  CH₂COOH obtained by the modification are preferably.

The chemical modification of the thiol group is conducted according to a method known per se as described, for example, in Textile Progress Vol. 7, page 1 (1975) by N. H. Leon, "Organic Sulfer Compounds" (1968) written by Shigeru Ooae and published by Kagaku Dojin Co., Ltd., and "Course of Polymer Experimentation" Vol. 12 (1957) written by Masami Oku and published by Kyoritsu Pub. Co.

The decomposition products of keratin and derivatives thereof have a molecular weight of 100 to 100,000, preferably 350 to 30,000.

Silk fibers which are one of the starting materials for the ingredient (B) may be used as a powder thereof or as a powder of a product obtained by washing and treating the same with acid. Preferably, silk fibers are used as a product obtained by hydrolysis with an acid, alkali or enzyme. The hydrolyzate of silk fibers may be obtained by hydrolysis with an acid such as hydrochloric acid, sulfuric acid, phosphoric acid or the like, and alkali such as sodium hydroxide, sodium carbonate or the like. Moreover, the acid or alkali hydrolysis may be used in combination with an enzyme hydrolysis. The resulting decomposition or hydrolysis product has a molecular weight of 100 to 100,000, preferably 350 to 30,000.

In the practice of the invention, the ingredient (B) is used in an amount of 0.1 to 10 wt %, preferably 0.1 to 5.0 wt %, of the hair cosmetic composition.

The mixing ratio of the ingredients (A) and (B) in the hair cosmetic composition of the invention is 0.1 to 10:1, preferably 1 to 8:1.

The term "hair cosmetic or cosmetics" used herein is intended to mean all cosmetics applicable to the hair. For instance, there are included pre-shampoo treatment agents, shampooes, hair rinses, after shampoo agents, conditioners, hair conditioners, setting lotions, blow styling lotions, hair sprays, hair dyes, bleaches, first permanent waving solutions, second permanent waving solutions, hair liquids, hair tonics and the like.

The hair cosmetic compositions according to the invention are prepared by adding the essential ingredients (A) and (B) to known ingredients for these purpose which may vary depending on the type of hair cosmetic. The hair cosmetic composition may be formulated in various forms such as aqueous solution, ethanolic solution, emulsion, suspension, gel, solid, aerosol, powder and the like.

Preparation of the hair cosmetics of the invention are described.

(1) Shampoo

Prepared by mixing known shampoo constituents by a usual manner along with one or more anionic active agents and the ingredients (A) and (B).

Preferable anionic active agents which are used as a shampoo substrate are mentioned below.

(1) Linear or branched alkylbenzenesulfonates having an alkyl group having from 10 to 16 carbon atoms on average.

(2) Polyoxyalkylene alkylsulfates having a linear or branched alkyl group having from 8 to 20 carbon atoms on average and added with 0.5 to 8 moles, on average, of ethylene oxide and/or propylene oxide in one molecule thereof.

(3) Alkylsulfates having an alkyl group having from 10 to 20 carbon atoms on average.

(4) Olefinsulfonates having from 10 to 20 carbon atoms on average in one molecule thereof.

(5) Alkanesulfonates having from 10 to 20 carbon atoms in one molecule thereof.

(6) Alkylethoxycarboxylates having an alkyl group having from 10 to 20 carbon atoms on average and added with from 0.5 to 8 moles of ethylene oxide on average in one molecule thereof.

(7) Succinic acid derivatives represented by the following formula $$R_1-\underset{\underset{CH_3COOY_1}{|}}{CHCOOX_1}$$

(in which $R_1$ represents an alkyl group or alkenyl group having from 6 to 20 carbon atoms, $X_1$ and $Y_1$ independently represent an ion).

Counter ions of these anionic active agents are, for example, alkali metal ions such as sodium, potassium and the like, alkaline earth metal ions such as calcium, magnesium and the like, ammonium ions, and alkanolamines having from 1 to 3 alkanol group having 2 or 3 carbon atoms and including, for example, monoethanolamine, diethanolamine, triethanolamine, triisopropanolamine and the like.

Of these anionic active agents, linear or branched alkylsulfates having from 10 to 16 carbon atoms on average, polyoxyethylene alkylsulfates (an average number of addition moles of 0.5 to 8) having an alkyl group having from 8 to 20 carbon atoms on average, and olefinsulfonates having from 10 to 16 carbon atoms on average are preferably used.

In the shampoo compositions of the invention, anionic active agents are generally used in an amount of from 5 to 30%, preferably 10 to 25%.

Other ingredients may be used in the shampoo composition of the invention in amounts not to impede the effect of the invention, which include amphoteric active agents, nonionic active agents, cationic active agents, solubilizers such as propylene glycol, glycerine, urea and the like, viscosity adjusters such as ethyl alcohol, isopropyl alcohol, hydroxyethyl cellulose, methyl cellulose, higher alcohols and the like, perfumes, colorants, UV absorbers, antioxidants, preservatives, pearling agents, lotionizing agents, and the like. These agents may be added as desired.

The thus obained shampoo composition not only has excellent hair-conditioning and washing effects, but also is less irritative than known shampooes when it comes in contact with eyes by mistake upon washing and rinsing, giving only a mild influence on the conjunctiva and the iris.

(2) Hair rinses, hair conditioners, hair treatments

The ingredients (A) and (B) are dissolved or dispersed in a suitable solvent or medium such as water, ethanol, glycerin, ethylene glycol, propylene glycol, 1,3-propanediol, isopropanol, polyethylene glycol or the like, thereby obtaining the rinse, conditions or treatment composition.

To these compositions, may be further added any known ingredients which are ordinarily used in rinses, conditioners or treatments. Preferable ingredients which are added to the compositions are surface active agents such as cationic active agents, anionic active, nonionic active agents and amphoteric active agents. Most preferably, cationic active agents should be added.

Specific examples of the surface active agents are mentioned below.

(a) Anionic active agents (1) Linear or branched alkylbenzenesulfonates having an alkyl group having from 10 to 16 carbon atoms on average.

(2) Alkyl or alkenyl ethoxysulfates having a linear or branched alkyl or alkenyl group having from 8 to 20 carbon atoms on average and having 0.5 to 8 moles, on average, of ethylene oxide added in one molecule thereof.

(3) Alkyl- or alkenylsulfates having an alkyl or alkenyl group having from 10 to 20 carbon atoms on average.

(4) Olefinsulfonates having from 10 to 20 carbon atoms on average in one molecule thereof.

(5) Alkanesulfonates having from 10 to 20 carbon atoms on average in one molecule thereof.

(6) Saturated or unsaturated aliphatic acid salts having from 10 to 20 carbon atoms on average in one molecule thereof.

(7) Alkyl or alkenyl ethoxycarboxylates having an alkyl or alkenyl group having from 10 to 20, preferably 12 to 16, carbon atoms on average and having 0.5 to 8 moles, on average, of ethylene oxide added in one molecule thereof.

(8) Alpha-sulfofatty acid salts or esters represented by the following formula $$R_2CHCO_2Y_2$$
$$|$$
$$SO_3M_1$$

in which $Y_2$ represents an alkyl group having from 1 to 3 carbon atoms or a counter ion, $M_1$ represents a counter ion, $R_2$ respresents an alkyl or alkenyl group having from 10 to 20, preferably 12 to 16, carbon atoms.

The counter ions of the anionic active agents are, for example, alkali metal ions such as sodium, potassium and the like, alkaline earth metal ions such as calcium, magnesium and the like, ammonium ions, and alkanolamines having from 1 to 3 alkanol groups having 2 or 3 carbon atoms and including, for example, monoethanolamine, diethanolamine, triethanolamine, triisopropanolamine and the like.

(b) Nonionic active agents (1) Polyoxyethylene alkyl or alkenyl ethers having a primary or secondary alkyl or alkenyl group having from 8 to 20 carbon atoms on average and having from 3 to 12 moles of ethylene oxide added thereto.

(2) Polyoxyethylene alkylphenyl ethers having an alkyl group having from 8 to 12 carbon atoms on average and having from 3 to 12 moles of ethylene oxide added thereto.

(3) Higher fatty acid alkanolamides represented by the following formula and alkylene oxide adducts thereof

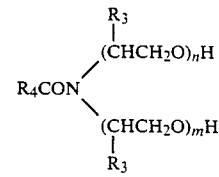

in which $R_3$ represents H or $CH_3$, $R_4$ represent an alkyl or alkenyl group having from 10 to 20 carbon atoms, n is an integer of from 1 to 3, and m is an integer of from 0 to 3.

(c) Amphoteric active agents (1) Alkylamine oxides represented by the following formula

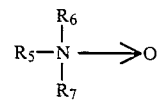

in which $R_5$ represents an alkyl or alkenyl group having from 10 to 20 carbon atoms, $R_6$ and $R_7$ independently represent an alkyl group having from 1 to 3 carbon atoms and may be the same of different.

In the above formula, it is preferred the $R_5$ represents an alkyl or alkenyl group having from 12 to 16 carbon atoms and $R_6$ and $R_7$ independently represent methyl group.

(2) Compounds of the following formula

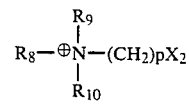

in which $R_8$ represents an alkyl or alkenyl group having from 10 to 20 carbon atoms, $R_9$ and $R_{10}$ independently represent an alkyl group having from 1 to 4 carbon atoms, p is an integer of from 1 to 3, and $X_2$ represents a $COO^-$ or $-SO^-$ group. Preferably, $R_8$ represents an alkyl or alkenyl group having from 12 to 16 carbon atoms, $R_9$ and $R_{10}$ independently represent methyl group, and p is an integer of 3.

(3) Imidazoline compounds represented by the following formula

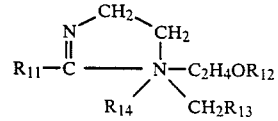

in which $R_{11}$ represents a fatty acid residue having from 10 to 20 carbon atoms on average, $R_{12}$ represents hydrogen, Na or $CH_2COOMe$ in which Me represents H, Na or an organic base, $R_{13}$ represents COOMe, $CH_2COOMe$ or

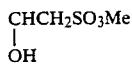

in which Me has the same meaning as defined above, and $R_{14}$ represents a hydroxyl group, an acidic salt, or an anionic active sulfate or sulfonate. Preferably, $R_{11}$ represents a fatty acid residue having from 12 to 16 carbon atoms.

(d) Cationic active agents

In the practive of the invention, any cationic active agents may be used without limitation so far as they are ordinarily used in hair rinses or the like. Preferable examples of the agents include quaternary ammonium salts represented by the following formula (1)

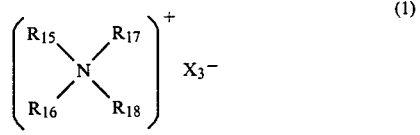

in which one or two of $R_{15}$, $R_{16}$, $R_{17}$ $R_{18}$ independently represent a long-chained alkyl group or long-chained hydroxyalkyl group having from 8 to 20 carbon atoms, and the others independently represent an alkyl or hydroxyalkyl group having from 1 to 3 carbon atoms or a benzyl group, and $X_3$ represents a halogen atom or an alkyl sulfate group having from 1 or 2 carbon atoms. Specific examples of the quaternary ammonium salts are distearyldimethylammonium chloride, stearyltrimethylammomium methosulfate, stearyltrimethylammonium chloride, stearyldimethylbenzylammonium thloride, lauryldiethylbenzylammonium chloride, lauryltrimethlammonium bromide, distearylmethylhydroxymethyl chloride, cetyltrimethylammonium chloride and the like.

Good results are obtained using these surface active agents in an amount of 0.01 to 10%, preferably 0.5 to 5%, of the hair rinse composition.

The hair rinse or the like composition of the invention may further comprise hydrocarbons such as liquid paraffin, Vaseline ® Petroleum Jelly, solid paraffin and the like, esters such as isopropyl myristate, lanolin derivatives such as lanolin, refined lanolin, lanolin fatty acids and the like, silicone derivatives such as dimethylpolysiloxane, methylphenylpolysiloxane, organomodified polysiloxane and the like, polyethylene glycol, polypropylene glycol or polymers thereof, oils such as polyoxyalklene alkyl ether, polyoxyalkylene alkyl ether phosphates and the like, polymeric materials such as hydroxyethyl cellulose, hydroxypropyl cellulose, hydroxpropylmethyl cellulose, methyl cellulose, cationized cellulose, cationized polymers and the like, bactericides. preservatives, perfumes, colorants and the like.

(3) Hair Setting Agents (setting lotions, hair sprays and the like)

The ingredients (A) and (B) are dissolved, as usual, in polar solvents such as water, ethyl alcohol, propyl alcohol and the like, thereby obtaining hair setting agents. Any polymer compounds which are used in ordinary hair setting agents may also be used in the practice of the invention. Examples of such polymer compounds are mentioned below.

(a) Polyvinylpyrrolidone compounds

Specific examples of these compounds include polyvinylpyrrolidone, copolymers of vinylpyrrolidone and vinyl acetate, copolymers of vinylpyrrolidone, vinyl acetate and alkylaminoacrylates, and the like. These compounds are commercially available under the names of Luviskol K, Luviskol VA, Luviflex D410I (Yuka Badische Co., Ltd.), and PVPK, PVP/VA and E-735 (GAF Co., Ltd.).

(b) Acidic vinyl ether polymer compounds

For instance, there are mentioned lower alkyl half-esters of copolymers of methyl vinyl ether and maleic anhydride, which are commerically available under the names of Gantrez ES-225 and ES-335 (Gaf Co., Ltd.).

(c) Acidic polyvinyl acetate polymer compounds

Examples of these compounds include copolymers of vinyl acetate and crotonic acid and are commercially sold under the names of Resin 28-1310 (National Starch Co., Ltd.), Luviset CE5055 (Yuka Badische Co., Ltd.).

(d) Acidic acrylic polymer compounds

For instance, copolymers of acrylic acid and/or methacrylic acid and alkyl acrylates and/or alkyl methacrylates, and copolymers of acrylic acid, alkyl acrylates and N-alkylamides are mentioned. Commercial products include Plasize (Gooh Chem. Co., Ltd.), Ultrahold (Ciba-Geigy A. G.), and the like (e) Amphoteric acrylic polymer compounds There are mentioned compounds which are obtained by copolymerizing dialkylaminoethyl methacrylates, dialkylaminoethyl arylates or diacetone acrylamides with acrylic acid, methacrylic acid, alkyl acrylates and alkyl methacrylates and subjecting the copolymers to amphoteric reaction with halogenated acetic acid. Yuka Foamer AM-TS (Mitsubishi Petrochemical Co., Ltd.) is typical of commerical products of these polymer compounds.

The hair setting agents of the invention may further comprise, within ranges of amounts not impending the effect of the invention, arbitrary ingredients which may depend on the purpose. Examples of such arbitrary ingredients include oil substance such as higher alcohols, higher fatty acid acid esters, and the like, nonionic active agents serving as an emulsifier or solubilizer such as polyoxyethylene lauryl ether, polyoxyethylene sorbitan monolaurate, polyoxyethylene hardened castor oil, and the like, humectants such as glycerine, propylene glycol and the like, perfumes, colorants, and the like.

The hair setting agents of the invention may be applied to the hair as they are. Alternatively, they may be applied in the form of mist by the use of a pump sprayer or the like or may be applied in the form of mist of foam after packed ina container along with a jetting agent such as flon gas, liquid hydrocarbons or carbon dioxide gas.

The thus obtained hair setting agents of the invention can form a uniform, tough film after drying, which shows excellent hair setting ability even under high humidity conditions. These hair setting agents can be readily removed from the hair upon washing it with now widely used shampooes comprising anionic active agents. Thus, the hair setting agents of the invention satisfy both requirements of set retentivity and washability.

(4) First permanent waving agents

The agents can be prepared by mixing the ingredients (A) and (B) with an ordinary permanent waving solution comprising a reducing material as a substrate.

The reducing materials which are used as a substrate of the first permanent waving agent may be any known materials which are ordinarily used for the purposes. Preferable examples include ammonium salts of thioglycollic acid and hydrochlorides of cysteine.

The first permanent waving agent may be prepared by mixing the above ingredients together by any known technique. The waving agent may further comprise conventionally used ingredients such as colorants, perfumes, oils, opacifiers, water-soluble silicones, organic salts, urea and the like. These ingredients are used depending on the purpose.

(5) Second permanent waving agents

To ordinary second permanent waving agents comprising oxidative materials as a substrate are added the ingredients (A) and (B).

The amount of an oxidative material which is used as a substrated of the second permanent waving agent of the invention may differ depending on whether or not the second agent is dissolved in solvent, or the degree of dilution when such an agent is used as diluted. The amount is generally in the range of from 1 to 30%, preferably from 3 to 20%.

The oxidative materials which are used as a substrate of the second permanenet waving agent may be any materials ordinarily used for the purposes and include, for example, alkali metal bromates such as sodium bromate, potassium bromate and the like, hydrogen peroxide, sodium percarbonate, sodium perborate and the like. Of these, alkali metal bromates are perferred.

The second permanent waving agents may further comprise, aside from the above essential ingredients, arbitrary ingredients used for the purposes in amounts not impeding the effect of the invention. Examples of such arbitrary ingredients include anionic active agents, amphoteric active agents, nonionic active agents, cationic polymer compounds, water-soluble silicones, urea, suitable oils, humectants, perfumes, colorants and the like.

Cationic polymer compounds mentioned above are, for example, cationic cellulose derivatives, cationic starch, diallyl quaternary ammonium salts, copolymers of diallyl quaternary ammonium salts and acrylamide, polyglycol and polyamide condensates, methacryloxyethyltrimethylammonium salts, and copolymers of metharyloxyethyltrimethylammonium salts and polyvinyl pyrrolidone. Of these, there are preferably used cationic cellulose a typical product of which is available under the name of "Polymer JR", diallyl quaternary ammonium salts a typical product of which is available under the name of "Merquat 100", and diallyl quarternary ammonium salt/acrylamide copolymer typical of which is a product available under the name of "Merquat 550". These cationic polymer compounds are generally used in an amount of from 0.01 to 5%, preferably 0.05 to 2%.

The thus obtained second agent is adjusted in such a way that an aquenous 5% solution thereof has a pH of below 9, preferably from 3.5 to 6.5.

(6) Hair dyes

The ingredients (A) and (B) are added to dye substrates as usual to give hair dyes.

The dye substrates used in the hair dye composition of the invention are not critical and include any known substrates. For example, oxdiation hair dyes and temporary dyes are described by way of illustration only.

(i) Oxidation hair dyes

Dye intermediates, oxidizing agents and, if necessary, couplers or modifiers are mixed together.

Examples of the dye intermediates include para or ortho compounds such as p-phenylenediamine, toluene-2,5-diamine, N-phenyl-p-phenylenediamine, 4,4'-diaminodiphenylamine, p-aminophenol, p-methylaminophenol, o-phenylenediamine, toluene-3,4-diamine, o-aminophenol, p-chloro-o-phenylenediamine, p-amino-o-cresol, o-chloro-p-phenylenediamine, phloroglucin pyrogallol, 3,3'-iminodiphenyl, diphenylamine, 2,6-diaminopyridine, p-aminophenylsulfamic acid and the like. Couplers or nodifiers include metha compounds or phenols such as m-phenylenediamine, toluene-2,4-diamine, p-methoxy-m-phenylenediamine, m-aminophenol, alpha-naphthol, resorcin, hydroquinone, catechol and the like. Hydrogen peroxide is ordinarily used as the oxidizing agent. Also, there may be used sodium perborate, urea peroxide, sodium percarbonate, sodium peroxytripolyphosphate, sodium peroxypyrophosphate, sodium peroxyorthophoshate, sodium silicate and hydrogen peroxide adduct, sodium sulfate-sodium chloride-hydrogen peroxide adduct, and the like. In order to give an influenence on the color of the hair without taking part in the dye formation reaction, there may be further added direct dyes and particularly nitro dyes such as nitro-p-phenyenediamine, p-nitro-o-phenylenediamine, 2-amino-4-nitrophenol, 2-amino-5-nitrophenol, 4-amino-2-nitrophenol and the like. If necessary, picramic acid, picric acid and/or 1,4-diaminoanthraqinone may be also added.

Within ranges of amounts not impeding the effect of the invention, there may be also added nonionic active agents, cationic active agents, solvents such as propylene glycol, glycerine and the like, viscosity adjusters including lower alcohols such as ethyl alcohol, isopropyl alcohol and the like, hydroxyethyl cellulose, methyl cellulose, cationic polymer compounds, and higher alcohols, humectants, protein modifiers such as urea, perfumes, colorants, UV absorbers, antioxidants, preservatives, pearling agents, lotionizing agents, and the like.

The oxidation hair agents of the invention are prepared by mixing the essential ingredients and the above-mentioned ingredients by a usual manner to give a powder preparation or a cream preparation. In applications, the preparation is added to water or a shampoo substrate. Alternatively, an oxidation dye and an oxidizing agent are separately provided. The essential ingreadients are added to either or both of the agents to give powder, cream or liquid preparation. In applications, separately provided systems are combined together.

(ii) Temporary hair dyes

Dyes and pigments are not limited to any specific ones and include, for example, pigments such as titanium oxide, carbon black and the like, and tar-base colorants such as triphenylmethane dyes, azo dyes, quinoline dyes, xanthene dyes, acridine dyes, azine dyes, oxazine dyes, indigoid dyes, stilbene dyes, thiazole dyes and the like.

The resins are, for example, copolymers of acrylic esters or methacrylic esters, copolymers of monochloroacetic acid-amine salt-modified products of N,N'-diethylaminoethyl methacrylate and metharylic esters, copolymers of vinyl pyrrolidone and vinyl acetate and the like.

The temporary hair dyes are prepared by dissolving or dispersing the essential ingredients, resins, dyes and pigments in a dispersion medium such as water, amyl alcohol, isopropanol, ethanol or acetone. As a matter of course, there may be further added known ingredients, which are ordinarily added to existing temporary hair dye compositions, including anionic active agents, cationic active agents, amphoteric active agents, nonionic active agents, polyhydric alcohols such as propylene glycol, glycerine, polyethylene glycol and the like, higher alcohols such as isostearyl alcohol, oleyl alcohol and the like, fatty acids such as lanolin fatty acids, fatty acids from coconut oil and the like, esters such as isopropyl myristate, hydrocarbons such as liquid paraffin, cationized polymer compounds, amines, perfumes, and the like.

(7) Pre-shampoo treatment agents

Pre-shampoo treatment agent is prepared by dissolving or suspending the ingredients (A) and (B) and, optionally, other known ingredients in a medium such as water.

Known ingredients are, for example, oils and fats such as higher alcohols, fatty acid esters and the like, nonionic active agents serving as an emulsifier or solubilizing agent and including polyoxyalkylene alkyl ethers, and humectants such as glycerine, pyrrolidonecarboxylic acid and the like. These ingredients serve to control a degree of styling of the hair when the hair is treated with the preshampoo treatment agent of the invention and shampooed thereafter. That is, of liquid oil or fat ingredients is effective in imparting softness to the hair and humectants can impart moistness to the hair. In addition, use of higher alcohols imparts dryness to the hair.

The present invention is described by way of references and examples, which should not be construed as limiting the present invention thereto.

Reference 1

Ten kilograms of the whole of a birch tree (Betula alba) was admixed with 20 liters of 40% 1,3-butylene glycol and immersed therein at 20° to 25° C. for 10 to 15 days, followed by centrifugal separation. To the residue was further added 10 liters of 1,3-butylene glycol for re-immersion. The resulting immersion solution and the solution obtained by the centrifugal separation were combined and aged in a dark and cold place (0° to 5° C.) for about 40 days. As a result, there was obtained a brich extract in the form of a dark brown liquid containing 5% solid matters.

Reference 2

Twenty liters of 50% ethanol was added to 10 kg of the whole of a birch tree (*Betula alba*) for immersion in a cold and dark place for 20 days. As a result, a birch extract in the form of a brown liquid containing 6.5% solid matters was obtained.

Reference 3

Ten liters of an aqueous 50% propylene glycol solution was added to 5 kg of leaves of rosemary (*Rosemarinus Officinalis*), followed by refluxing at 50° C. for 12 hours to obtain an extract. The extract was subjected to filtration to remove the residue therefrom to obtain a final product. This product was a rosemary extract in the form of a brown liquid containing 10% solid matters.

Reference 4

Ten kilograms of silk fibers obtained from the silkworm was washed with water, dried, cut into pieces, powdered and passed through a 200 microns sieve to obtain 9.5 kg of a silk powder.

Reference 5

Sixty grams of silk fibers were dissolved in 600 ml of water containing 48 g of ethylenediamine and 36 g of cupric hydroxide, followed by heating to 60° C. for 2 hours. Subsequently, the solution was adjusted in pH with 3H with 3N acetic acid to 6.0-7.0, and filtered, followed by placing the resulting filtrate in a cellulose tube C-65 and subjecting to dialysis in running water over one or two days and nights. The resulting dialyzate was filtered and made up to 2000 ml, to which was added 80 g of a strongly aicdic cationic exchange resin Dowex 50wx-2, followed by agitating for 20 to 30 minutes and filtering. Thereafter, the resulting filtrate was admixed with an 1N sodium hydroxide solution to adjust its pH to 6.0-7.0. As a result, there was obtained 1900 ml of a solution containing 0.5% of the effective ingredient. The thus obtained silk protein had an average molecular weight of 2000.

Reference 6

Preparation of Decomposition Derivatives by oxidation of Karatin Material:

Ten grams of wool fibers were immersed in 700 g of an aqueous 8% peracetic acid solution at room temperature for 1 day to carry out the oxidation reaction. The resulting oxidized wool fibers were filtered, washed with water and immersed in 700 g of a 0.1N ammoniacal solution at room temperature for 1 day, permitting about 90% of the wool to dissolve in the ammoniacal solution. About 1 g of the insoluble matters were removed by filtration and the aqueous ammoniacal solution of keratose to be an oxidized decomposition product of the wool keratin was admixed with 2N hydrochloric acid to adjust the pH to 4.0, whereupon alpha-keratose was settled as precipitate. This precipitate was filtered, washed with acetone and dried to obtain 5.4 g of alpha-keratose.

Reference 7

Keratin Materials:

Ten grams of wool fibers were immersed in 600 ml of an aqueous solution with concentration of 8M urea and 0.01M tris buffer, to which was added 6 ml of 2-mercaptoethanol, followed by adjusting the pH to 10 by means of a 5N potassium hydroxide aqueous solution to effect the reduction reaction in a stream of nitrogen at room temperature. About 3 hours after commencement of the reaction, the wool dissolved in the reaction solution in an amount of about 85% thereof. While the system was adjusted with a 5N potassium hydroxide solution so that the pH was not below 7, 16.5 g of iodoacetic acid was gradually added and the pH of the system was finally adjusted to 8.5 to carry out the carboxymethylation reaction at room temperature for 2 hours. The reaction solution was filtered to remove insoluble matters therefrom and the resultant filtrate was charged into a cellulose tube wherein it was dialyzed against ion-enchanged water to remove low molecular weight impurities including urea. As the urea was dialyzed, the content in the cellulose tube became cloudy since water-insoluble HGT (component with high contents of glycerine and tyrosine was cause to precipitate. After completion of the dialysis, HGT was centrifugally removed and S-carboxymethyl keratin (SCMKA) was obtained from the neutral transparent solution of SCMKA by the isoelectric precipitation method. That is, 1N hydrochloric acid was added to the system to adjust its pH to 4.4 by which SCMKA became insoluble and separated as precipitate. This precipitate was filtered, washed with ethanol and dried to obtain 4.2 g of SCMKA.

Reference 8
Preparation of Hydrolysis Derivatives of Keratin Materials:

Ten grams of wool fibers were immersed in 300 g of a 1% sodium hydrogensulfite aqueous solution, whose pH was adjusted to 6.7 by the use of a 5N aqueous caustic soda solution. Thereafter, 0.2 g of papain was added to the system to effect the hydrolysis reaction at 60° C. for 15 hours, by which about 80% of the wool dissolved. Insoluble matters were removed by filtration and the sulfite in the resulting filtrate was removed by the ultrafiltration technique using a membrane with a fractional molecular weight of 500. The aqueous solution of the hydrolysate was concentrated and freeze dried to obtain 7.7 g of the hydrolysate having a molecular weight of 500-2,000.

Example 1

Shampoo:

Evaluation Item

The degree of ease in passing fingers through the hair upon washing was evaluated as "foam smoothness".

Evaluation standard
O Better foam smoothness than that of a reference
  Slightly better than a reference
X Same in foam smoothness as a reference (3) Combing force Thirty grams of human hair was wetted with water of 40° C. to permit 20 g of water to be contained. One gram of each of the shampoo compositions was used to effect washing and rinsing operations two times, after which it was squeezed and set on a strain gauge. Subsequently, the hair was combed to determine a force exerted thereon (wetd combing force). The hair was then dried with a dryer and allowed to stand in a air-conditioned room of a temperature of 20° C. and a relative humidity of 65% overnight, followed by setting on a strain gauge and combing to determine a force exerted thereon (dry combing force).

(4) Hair fly

Upon the measurement of "combing force" under dry conditions, it was observed whether or not there took place an electrostatic hair fly phenomenon.

Evaluation
O Occurrence of hair fly
X No occurence of hair fly

TABLE 1-A

|  | A | B | C | D | E | F | G |
|---|---|---|---|---|---|---|---|
| Sodium polyoxyethylene (2) lauryl sulfate | 15% | 15% | 15% | 15% | 15% | 15% | 15% |
| Coconut fatty acid diethanolamide | 3 | 3 | 3 | 3 | 3 | 3 | 3 |
| Rosemarry extract (Novarom Co., Ltd.) | — | 0.5 | 0.5 | — | 0.5 | — | 0.5 |
| Oxidative decomposition product of keratin (obtained in Reference 6) | — | — | 0.1 | — | — | — | — |
| Oxidative decomposition product of collagen* | — | — | — | 0.1 | 0.1 | — | — |
| Hydrolyzed decomposition product of collagen** | — | — | — | — | — | 0.1 | 0.1 |
| Perfume | suitable amount | suitable amount | suitable amount | Suitable amount | Suitable amount | Suitable amount | Suitable amount |
| Water | balance (pH 7.2) | balance (pH 7.2) | balance (pH 7.2) | balance (pH 7.2) | balance (pH 7.2) | balance (pH 7.2) | balance (pH 7.2) |

*, **: having average molecular weight of about 1,000.

Shampoo compositions of the formulations indicated in Table 1-A were prepared and subjected to the performance evaluation test thereof. The results are shown in Table 1-B.

The performance evaluation was conducted according to the following methods in or throughout the examples appearing hereinafter.

(1) Lathering or foaming test

To an aqueous solution of 1% shampoo composition was added 0.1% of lanolin as an artificial dirt, followed by agitating in a cylinder for 5 minutes by means of a flat propeller at 40° C. at 1000 r.p.m. in such a way that the propeller was turned in opposite directions every 10 second. After completion of the agitation, añ amount of lathering after 30 seconds was measured for evaluation.

(2) Touch of lather

Thirty grams of human hair was wetted with water of 40° C. to permit 20 g of water to be contained. Thereafter, 1 g of each of the shampoo compositions was used for washing the hair therewith whereupon the touch of the lather was organoleptically evaluated by 20 female panelers.

TABLE 1-B

| | Lathering Characteristics | | Hair Finishing | |
|---|---|---|---|---|
| | Lathering | Lather Smoothness | Combing Force (g) | Hair Fly |
| A | 114 | X | 210 | O |
| B | 105 | Δ | 196 | O |
| C(product of invention) | 138 | ⊚ | 101 | X |
| D | 91 | X | 254 | O |
| E | 93 | Δ | 247 | O |
| F | 87 | X | 201 | O |
| G | 90 | X | 198 | O |

Example 2

Shampoo:

Shampoo compositions of the formulation indicated in Table 2-A were prepared and subjected to the performance evaluation test. The results are shown in Table 2-B.

The performance evaluations were effected in the same manner as in Example 1.

TABLE 2-A

|  | H | I | J |
|---|---|---|---|
| Sodium polyoxyethylene(2) lauryl sulfate | 15% | 15% | 15% |
| Coconut fatty acid diethanolamide | 3 | 3 | 3 |
| Birch extract (Novarom Co., Ltd.) | — | 0.5 | 0.5 |
| Hydrolyzate of silk (average molecular weight of 20,000) | — | — | 0.1 |
| Perfume | suitable amount | suitable amount | suitabe amount |
| Water | balance (pH 7.2) | balance (pH 7.2) | balance (pH 7.2) |

TABLE 2-B

| | Lathering Characteristics | | Hair Finishing | |
|---|---|---|---|---|
| | Lathering | Lather Smoothness | Combing Force (g) | Hair Fly |
| H | 114 | X | 210 | O |
| I | 107 | Δ | 176 | O |
| J (product of invention) | 142 | ◉ | 97 | X |

Example 3

Hair Rinse:

Hair rinses of the formulations indicated in Table 3-A were prepared. Five hundreds milliliters of a 50:1 dilution of each hair rinse was used to treat the hair therewith, which was subsequently rinsed with hot water two times and air-dried. The thus dried hair was evaluated by 20 panelers according to the following five-point method.

Evaluation standard:
Good 5, Fair 4, Moderate 3, Rather poor 2, Poor 1
The results are shown in Table 3-B as average values.

TABLE 3-A

|  | K | L | M | N |
|---|---|---|---|---|
| Distearyldimethyl-ammonium chloride | 2% | 2% | 2% | 2% |
| Stearyl alcohol | 1% | 1% | 1% | 1% |
| Birch extract (obtained in Reference 1) | — | 1% | — | 1% |
| Hydrolyzate of keratin (obtained in Reference 8, average molecular weight 3000) | — | — | 1% | 1% |
| Water | balance (pH 5.0) | balance (pH 5.0) | balance (pH 5.0) | balance (pH 5.0) |

TABLE 3-B

|  | Softness | Smoothness | Ease in Combing |
|---|---|---|---|
| K | 1.2 | 1.3 | 1.2 |
| L | 2.1 | 2.5 | 3.3 |
| M | 3.2 | 3.4 | 2.5 |
| N (product of invention) | 4.2 | 4.0 | 3.9 |

Example 4

Hair Rinse:

Hair rinses of the formulations indicated in Table 4-A were prepared and evaluated in the same manner as in Example 3. The results are shown in Table 4-B.

TABLE 4-A

|  | O | P | Q | R |
|---|---|---|---|---|
| Distearyldimethyl-ammonium chloride | 2% | 2% | 2% | 2% |
| Stearyl alcohol | 1% | 1% | 1% | 1% |
| Rosemarry extract (obtained in Reference 3) | — | 1% | — | 1% |
| Hydrolyzate of silk (average molecular weight 20,000) | — | — | 1% | 1% |
| Water | balance (pH 5.0) | balance (pH 5.0) | balance (pH 5.0) | balance (pH 5.0) |

TABLE 4-B

|  | Softness | Smoothness | Ease in Combing |
|---|---|---|---|
| O | 1.2 | 1.3 | 1.2 |
| P | 2.1 | 2.6 | 3.4 |
| Q | 3.2 | 3.4 | 2.5 |
| R (product of invention) | 4.5 | 4.1 | 4.4 |

Example 5

Hair Treatment Agent:

Hair treatment agents of formulations (S) through (V) were prepared using the following fundamental composition.

| Fundamental Composition | |
|---|---|
| Liquid paraffin | 5.0% |
| White vaseline petroleum jelly | 2.0% |
| Cetyl alcohol | 2.0% |
| POE(20)sorbitan monostearate | 1.0% |
| Glycerine | 10.0% |
| Water | balance pH 7.0 |

To the above composition were added:
(S) no material,
(T) 1.0% of a birch extract (obtained in Reference 1),
(U) 2.0% of a hydrolyzate of keratin (an average molecular weight of 20,000), or
(V) 1.0% of a birch extract (obtained in Reference 1) and 2.0% of a hydrolyzate of keratin (average molecular weight of 20,000).

These hair treatments were evaluated according to the five-point method with respect to the following items. Average values of the respective evaluation tests are shown in Table 5.

TABLE 5

|  | Organoleptic Evaluation | Combing Force (g) | |
|---|---|---|---|
|  |  | Wet State | Dry State |
| S | 2.0 | 420 | 360 |
| T | 2.0 | 405 | 351 |
| U | 2.3 | 326 | 265 |
| V (product of invention) | 4.6 | 116 | 107 |

Example 6

Hair Treatment Agent:

Based on the fundamental composition of Example 5, the following formulations (W)–(Z) were prepared.
(W) Nothing was added.
(X) 1.0% of a birch extract (obtained in Reference 1) was added.

(Y) 2.0% of a silk hydrolyzate (average molecular weight 20,000) was added.

(Z) 1.0% of a birch extract (obtained in Reference 1) and 2.0% of a silk hydrolyzate were added.

The resulting hair treatments were evaluated in the same manner as in Example 5 with the results shown in Table 6.

TABLE 6

|   | Organoleptic Evaluation | Combing Force (g) Wet State | Dry State |
|---|---|---|---|
| W | 2.0 | 420 | 360 |
| X | 2.0 | 405 | 351 |
| Y | 2.3 | 326 | 265 |
| Z (product of invention) | 4.4 | 123 | 115 |

Example 7

Hair Setting Lotion:

Hair setting lotions of the formulations indicated in Table 7-A were prepared and their set retentivity was evaluated. The results are shown in Table 7-B.

TABLE 7-A

|   | A | B | C |
|---|---|---|---|
| Ethanol | 10% | 10% | 10% |
| Birch extract (Vermin Co., Ltd.) | — | 2.0% | 2.0% |
| Hydrolyzate of wool keratin (average molecular weight 20,000) | — | — | 1.0% |
| Polyoxyethylene oleyl ether (EO 20) | 0.5% | 0.5% | 0.5% |
| Perfum | 0.1% | 0.1% | 0.1% |
| Water | balance | balance | balance |

$$\text{Set retentivity (\%)} = \frac{Lo - Lt}{Lo - Ls} \times 100$$

in which,

Lo = 14 cm,

Ls = a length (cm) of a curled hair immediately after suspension under 95% relative humidity conditions, Lt = a length (cm) of a curled hair 30 minutes after suspension of the hair under 95% R.H. conditions.

TABLE 7-B

|   | Set Retentivity |
|---|---|
| A | 53% |
| B | 60% |
| C (product of invention) | 76% |

Example 8

Hair Setting Lotions:

Hair setting lotions of the formulations indicated in Table 8-A were prepared to determine set retentivity in the same manner as in Example 7. The results are shown in Table 8-B.

TABLE 8-A

|   | D | E | F |
|---|---|---|---|
| Ethanol | 10% | 10% | 10% |
| Birch extract (Vermin Co., Ltd.) | — | 2.0% | 2.0% |
| Silk hydrolyzate (average molecular weight 20,000) | — | — | 1.0% |
| Polyoxyethylene oleyl ether (EO20) | 0.5% | 0.5% | 0.5% |
| Perfum | 0.1% | 0.1% | 0.1% |
| Water | balance | balance | balance |

TABLE 8-B

|   | Set Retentivity |
|---|---|
| D | 53% |
| E | 60% |
| F (product of invention) | 84% |

Example 9

First Permanent Waving Agent:

Permanent waving treatments were effected using first permanent waving agents of the formulation indicated in Table 9-A and a second permanent waving agent to determine a degree of waving, wave retentivity, adsorptivity, and feeling to the touch. The results are shown in Table 9-B.

Formulation:

TABLE 9-A

|   | G | H | I |
|---|---|---|---|
| (1) First permanent waving agent |   |   |   |
| Ammonium thioglycollate | 7% | 7% | 7% |
| Birch extract (Novarom Co., Ltd.) | — | 1% | 1% |
| Silk hydrolyzate (average molecular weight 1,500) | — | — | 2% |
| Water (ammoniacal solution for pH adjustment) | 93% | 92% | 90% |

| Second permanent waving agent: | |
|---|---|
| Sodium bromate | 5.0% |
| Water | 95.0% |

Test method:

(1) Measurement of a degree of waving and wave retentivity (i) A bundle of 20 human hairs were fixed to cylinders of a wave-measuring plate (in which a plurality of cylinders, each having a diameter of 2 mm and a length of 1.5 mm, were arranged in zigzag form in two rows). The bundle was immersed in the first agent of each of the formulations through at 30° C. for 10 minutes, followed by immersion in a second agent at 30° C. for 10 minutes. Thereafter, the immersed bundle was sufficiently rinsed with water and removed from the plate. A degree of waving in still water was calculated according to the following equation.

It should be noted that the hair used was a 20 cm long virgin hair which was washed with an aqueous solution of 0.5% of sodium lauryl sulfate and dried.

$$\text{Degree of waving (\%)} \frac{Xo - Zo}{Xo - Yo} \times 100$$

Xo: a length of the hair fixed between points a and b of one row of the zigzag cylinders which are distant from each other.

Yo: a distance between a and b.

Zo: a distance of the hair, fixed between the point a and b, in still water after removal from the measuring plate.

(ii) The hair used in (i) was slightly moved and washed while immersing in an aqueous solution of 0.5% sodium lauryl sulfate for 1 minute, followed by sufficiently rinsing and air drying for 1 day. The above procedure was repeated four times and, after the fifth washing, the hair was sufficiently rinsed. Thereafter, a distance, Zo, in still water was measured, from which a degree of wave was determined. A ratio of this degree to a degree of wave prior to washing was was calculated to give a wave retentivity.

$$\text{Wave retentivity (\%)} \frac{\text{degree of wave after fifth washing}}{\text{degree of wave prior to washing}} \times 100$$

(2) Adsorptivity

The hair used for the measurement of the degree of wave was observed through a scanning electron microscope in order to determine the presence or absence of adsorbed matters on the hair surfaces. The evaluation standard is shown below.

| Adsorptivity | State of Hair Surfaces |
| --- | --- |
| ++ | Covered with a film and being thus smooth. |
| + | Slight amounts of adsorbed matters observed though the surfaces are smooth. |
| − | Considerable irregularities observed with hair cuticle being partly separated. |

(3) Evaluation of Feeling to the Touch

A hair bundle made of Japanese virgin hairs was immersed in a first agent of each of formulations through at 30° C. for 10 minutes and subsequently immersed in a second agent at 30° C. for 10 minutes. The bundle which was sufficiently rinsed with water and air/dried was evaluated by 20 female panelers according to the five-point method with respect to the feeling of the hair bundle to the touch. The evaluation standard was as follows: Good=5; Fair=4; Moderate=3; Rather poor=2; Poor=1. The results are indicated by geometric average.

TABLE 9-B

| First Permanent | Adsorptivity | Degree of wave (5) | Wave Retentivity (%) | Feeling to the touch |
| --- | --- | --- | --- | --- |
| G | − | 52 | 73 | 2.4 |
| H | + | 49 | 70 | 2.1 |
| I | ++ | 56 | 91 | 3.5 |

Example 10

Second Permanent Waving Agent:

The hair was permed using a first agent and second agents of the fomulations indicated below. A degree of damage of the hair during the perming treatment was determined by measuring weight of the hair prior to and after the treatment. The method of measuring the hair weight and the evaluation standard are described below.

[Composition]

| First Agent: | |
| --- | --- |
| Thioglycollic acid | 7.0% |
| Polyoxyethylene hardened castor oil | 1.0% |
| Perfume | 0.2% |

-continued

| First Agent: | |
| --- | --- |
| Ammoniacal solution, water | balance |

(pH adjusted to 9.0 by means of ammoniacal solution)

TABLE 10

| | Second Agents | | |
| --- | --- | --- | --- |
| | J | K | L |
| Sodium bromate | 5% | 5% | 5% |
| Amphoteric active agent (Miranol CSM-SF, by Miranol Co., Ltd.) | 0.5% | 0.5% | 0.5% |
| Perfume | 0.1% | 0.1% | 0.1% |
| Rosemarry extract (Vermin Co., Ltd.) | — | 1.0% | 1.0% |
| Silk hydrolyzate (average molecular weight 1,500) | — | — | 2.0% |
| Water | balance | balance | balance |

[Measurement of Hair Weight]

Ten centimeters long virgin hair was washed with an aqueous solution of 0.5% sodium lauryl sulfate and air-dried to give a hair being tested. About 1 g of the hair was bundled and placed in a desiccator using a phosphorus pentaoxide dryer, followed by drying under reduced pressure for one week and measuring the dried hair to give an absolute dry weight of the virgin hair. The thus dried hair was immersed in the first agent or solution at 30° C. for 10 minutes and sufficiently washed with water. Thereafter, the hair was further immersed in the respective second agents at 30° C. for 10 minutes. After sufficiently rinsing with water, it was air-dried and dried according to the above procedure to give an absolute dry weight of the permed hair.

[Evaluation Standard]

| Evaluation | Content |
| --- | --- |
| ⊚ | The difference in absolute dry weight between the virgin hair and the permed hair is less than 1%. |
| O | The difference in absolute dry weight between the virgin hair and the permed hair is in the range from 1 to 5%. |
| X | The difference in absolute dry weight between the virgin hair and the permed hair is over 5%. |
| Results | |
| J | X |
| K | O |
| L (product of invention) | ⊚ |

Example 11

Hair Dye:

Two-component hair dye compositions of the formulations indicated in Table 11 were prepared and the influence of these compositions on the hair was determined by measuring hair weights prior to and after the hair dyeing treatment. The results are shown below.

Composition:

TABLE 11

| | First Liquid Component | | |
| --- | --- | --- | --- |
| | M | N | O |
| p-Phenylenediamine | 1.0% | 1.0% | 1.0% |
| Birch extract (obtained in Reference 2) | — | 1.0% | 1.0% |

TABLE 11-continued

| | First Liquid Component | | |
|---|---|---|---|
| | M | N | O |
| Silk hydrolyzate (average molecular weight 20,000) | — | — | 0.5% |
| Propylene glycol | 10.0% | 10.0% | 10.0% |
| Disodium edetoate | 0.3% | 0.3% | 0.3% |
| Sodium sulfite | 0.5% | 0.5% | 0.5% |
| Perfume | 0.1% | 0.1% | 0.1% |
| Water | balance | balance | balance |

(pH was adjusted to 10.0 by means of an ammoniacal solution.)
(Second liquid component)

Evaluation Method:

Ten centimeters long virgin hair was washed with an aqueous solution of 0.5% sodium lauryl sulfate and air-dried to give a hair being tested. About 1 g of the hair was bundled and placed in a desiccator using phosphorus pentaoxide dryer, followed by drying under reduced pressure for 1 week and measuring the dried hair weight to give an absolute dry weight of the virgin hair.

Subsequently, the hair was dyed according to the following procedure and air-dried, followed by drying in the same manner as described above and measuring the weight of the dyed hair to give an absolute dry weight of the dyed hair.

The hair weight after the hair dyeing treatment was evaluated by comparison with the virgin hair weight and an influence of the respective dye compositions on the hair was judged.

[Evaluation Standard]

| Evaluation | Content |
|---|---|
| ⊚ | The dyed hair increased in weight over the virgin hair. |
| O | The dyed hair decreased in weight by 0–3% as compared with the virgin hair |
| X | The dyed hair decreases in weight over 3% as compared with the virgin hair. |

Dyeing Procedure:

A mixture of the first and second liquids in equal amounts was provided as a dyeing solution and was dilated to have a liquor ratio of 1:5. The hair was immersed in the solution at room temperature for 30 minutes and dyed. Thereafter, the hair was washed with city water of 40° C. to wash away the deposited dye therefrom and washed further with an aqueous solution of 0.5% sodium lauryl sulfate, followed by instantaneously immersing in an aqueous 1N acetic acid solution and washing in city water of 40° C.

Results:

| M | X |
|---|---|
| N | O |
| O (product of invention) | ⊚ |

Example 12

Hair Dye:

Temporary hair dye compositions (hair colorants) of the mascara type having formulations indicated in Table 12-A were prepared. 0.5 g of each composition was applied to 1 g of grey hair. After drying in air, the hair was organoleptically evaluated by 10 expert panelers with respect to the gloss, smoothness and feeling. The results are shown in Table 12-B.

Composition:

TABLE 12-A

| | P | Q | R |
|---|---|---|---|
| Polymer resin* | 12.0% | 12.0% | 12.0% |
| Pigment (carbon black) | 1.0% | 1.0% | 1.0% |
| Birch extract (obtained in Reference 1) | — | 1.0% | 1.0% |
| Silk hydrolyzate (average molecular weight 20,000) | — | — | 0.5% |
| Perfume | 0.1% | 0.1% | 0.1% |
| Ethanol | balance | balance | balance |

*Polymer resin: Copolymer of monochloroacetic acid-amine salt-modified product of N,N'—dimethylaminoethyl metharylate and methacrylic ester.

Results:

TABLE 12-B

| | Gloss | Smoothness | Feeling to the Touch |
|---|---|---|---|
| P | X | X | X |
| Q | Δ | Δ | O |
| R (product of invention) | O | O | O |

Example 13

Hair Liquid:
[Composition]

| (a) | Rosemary extract (Novarom Co., Ltd.) | 1.0% |
|---|---|---|
| (b) | Oxidative decomposition product of keratin (obtained in Reference 6) | 0.1% |
| (c) | Polyoxypropylene(30) butyl ether | 15.0% |
| (d) | Ethanol | 40.0% |
| (e) | Water | 44.0% |

[Preparation]

The above ingredients (a) through (e) were mixed together to completely dissolve the components to obtain a hair liquid.

Example 14

Hair Tonic: [Composition]

| (a) | Rosemary extract (obtained in Reference 3) | 1.0% |
|---|---|---|
| (b) | Hydrolyzate of keratin (obtained in Reference 8) | 0.1% |
| (c) | PCA-Al | 0.5% |
| (d) | Ethanol | 55.0% |
| (e) | Water | 44.0% |

[Preparation]

The above ingredients (a) through (e) were mixed and agitated until a uniform soultion was obtained, thereby giving a hair tonic.

Example 15

Hair Liquid:
[Composition]

| (a) | Birch extract (obtained in Reference 1) | 1.0% |
|---|---|---|
| (b) | Silk hydrolyzate (average molecular weight 20,000) | 0.1% |
| (c) | Polyoxypropylene(30) butyl ether | 15.0% |
| (d) | Ethanol | 40.0% |

-continued

| | |
|---|---|
| (e) Water | 44.0% |

[Preparation]
The above ingredients (a) through (e) were mixed for complete dissolution to obtain a hair liquid.

Example 16

Hair Tonic:
[Composition]

| (a) | Birch extract (Novarom Co., Ltd.) | 1.0% |
|---|---|---|
| (b) | Silk hydrolyzate (average molecular weight 20,000) | 0.1% |
| (c) | PCA-Al | 0.5% |
| (d) | Ethanol | 55.0% |
| (e) | Water | 44.0% |

[Preparation]
The above ingredients (a) through (e) were mixed and agitated until a uniform solution was obtained, thereby giving a hair tonic.

Example 17

Setting Lotion:
Setting lotions having formulations indicated in Table 17-A were prepared and applied to the hair to determine the feeling of the hair to the touch and set retentivity. The results are shown in Table 17-B.

TABLE 17-A

| | S | T | U |
|---|---|---|---|
| Birch extract (Dragoco Co., Ltd.) | — | 0.005% | 0.005% |
| Oxidative decomposition product of keratin (obtained in Reference 6) | — | — | 0.2% |
| Cationic polymer (Polymer JR400) | 1.0 | 1.0 | 1.0 |
| Sodium chloride | 1.0 | 1.0 | 1.0 |
| Ethanol | 5.0 | 5.0 | 5.0 |
| Water | balance | balance | balance |
| pH | 7.0 | 7.0 | 7.0 |

[Test Method]
(1) Feeling of Treated Hair to the Touch
Twenty grams of a 20 cm long hair bundle made of Japanese female hair was applied with 2 g of a hair cosmetic throughout the hair and then rinsed with running water of 40° C. for 1 minute. The thus treated hair was organolepitcally evaluated. The organoleptic evaluation was carried out by paired comparison according to the following evaluation point using, as a reference, a hair bundle treated with a commmercial hair rinse comprising as its principal components a quaternary ammonium salt and a hydrocarbon. An average point by 20 expert panelers is indicated in Table appearing hereinafter.

| Evaluation Point | Evaluation |
|---|---|
| +2 | Better in feeling than the reference hair bundle. |
| +1 | Slightly better than the reference hair bundle. |
| 0 | Equal to the reference hair bundle. |
| −1 | Slightly poorer than the reference hair bundle. |
| −2 | Poorer than the reference hair bundle. |

(2) Set-retaining Effect
A 20 cm long hair bundle having a weight of 5 g and made of Japanese female hair was applied with 1 g of a hair cosmetic throughout the hair and rinsed with running water of 40° C. for 1 minute, after which an excess of water was removed by means of filter paper. The thus treated hair bundle was wound around a glass tube with a diameter of 1.5 cm so that a winding width was 5 cm, and fixed at opposite ends thereof. The bundle was allowed to stand under conditions of 65 R.H. % and 20° C. for 24 hours and curled. After 24 hours, the wound bundle was removed from the tube and vertically suspended, whereupon its length was measured and a degree of curling was calculated according to the following equation.

$$\text{Degree of curling (\%)} = \frac{Ao - (Bo - Ao)}{Ao} \times 100$$

Ao: Length of the hair immediately after removal of the hair.
Bo: Length of the hair 12 hours after removal of the hair.

(3) Measurement of combing force under wetting conditions
After completion of the evaluation of the feeling of the hair, it was fixed on a strain gauge, through which a nylon comb was passed 20 times while recording a force exerted upon the comb. An average value of the 20 measurement was determined as a combining force.

(4) Feeling and measurement of combing force under dry conditions
The hair bundle after the measurement of the combing force under wet conditions was dried in air and then evaluated according to the evaluation and measurement methods described in (1) and (3) above.

Results:

TABLE 17-B

| | | | Combing Force | |
|---|---|---|---|---|
| | Feeling of the Hair | Degree of Curling | under wet conditions | under dry conditions |
| S | −0.1 | 72% | 170(g) | 194(g) |
| T | +0.1 | 76% | 165 | 187 |
| U | +1.4 | 90% | 107 | 160 |

Example 18

Setting Lotion:
Setting lotions of formulations indicated in Table 18-A were prepared and applied to the hair. The feeling of the hair and the set-retaining effect of the respective lotions were determined in the same manner as in Example 17. The results are shown in Table 18-B.

TABLE 18-A

| | V | W | X |
|---|---|---|---|
| Birch extract (Dragoco Co., Ltd.) | — | 0.005% | 0.005% |
| Silk hydrolyzate (M.W. 20,000) | — | — | 0.2% |
| Cationic polymer (Polymer JR400) | 1.0 | 1.0 | 1.0 |
| Sodium chloride | 1.0 | 1.0 | 1.0 |

TABLE 18-A-continued

|  | V | W | X |
|---|---|---|---|
| Ethanol | 5.0 | 5.0 | 5.0 |
| Water | balance | balance | balance |
| pH | 7.0 | 7.0 | 7.0 |

Results:

TABLE 18-B

|  |  |  | Combing Force | |
|---|---|---|---|---|
| | Feeling of the Hair | Degree of Curling | under wet conditions | under dry conditions |
| V | −0.1 | 72% | 170(g) | 194(g) |
| W | +0.1 | 76% | 165 | 187 |
| X | +1.3 | 93% | 136 | 161 |

What is claimed is:

1. A hair cosmetic composition consisting essentially of:
   (A) 0.001 to 10.0 wt. % of an extract obtained by extracting a plant selected from the group consisting of bark of birch and entire grass of rosemary with water or an aqueous solution containing an effective amount of one or more polar solvents selected from the group consisting of methanol, ethanol, propyleneglycol, 1,3-butyleneglycol and glycerine; and
   (B) 0.1 to 5.0 wt. % of a polypeptide compound selected from the group consisting of hydrolyzates of silk, hydrolyzates of keratin, oxidative decomposition products of keratin and thiol group-modified compounds of reductive decomposition products of keratin, and wherein said hair cosmetic composition is selected from the group consisting of pre-shampoo treatment agents, shampoos, hair rinses, hair conditioners, hair setting lotions, and hair sprays.

2. The hair cosmetic composition of claim 1, wherein said extract is present in the amount of 0.01–1.0 wt. %.

3. The hair cosmetic composition of claim 1, wherein said silk hydrolyzates and said keratin hydrolyzates and decomposition products have a molecular weight of 100 to 100,000.

4. The hair cosmetic composition of claim 3, wherein said silk hydrolyzates and said keratin hydrolyzates and decomposition products have a molecular weight of 350 to 30,000.

5. The hair cosmetic composition of claim 1, wherein (A) and (B) are mixed in a ratio of 0.1–10:1, respectively.

6. The hair cosmetic composition according to claim 1, which is a shampoo which further contains, in addition to ingredients (A) and (B), an effective amount of one or more surface active agents selected from the group consisting of anionic surface active agents, nonionic surface active agents and amphoteric surface active agents.

7. The hair cosmetic composition according to claim 1, which is a hair setting lotion which further contains, in addition to ingredients (A) and (B), one or more polymers selected from the group consisting of polyvinylpyrrolidone polymers, acidic vinyl ether polymers, acidic acrylic polymers and amphoteric acrylic polymers.

8. The hair cosmetic composition according to claim 1, further comprising a quaternary ammonium salt selected from the group consisting of distearyldimethyl ammonium chloride, stearyltrimethyl ammonium methosulfate, stearyltrimethyl ammonium chloride, stearyldimethylbenzyl ammonium chloride, lauryldiethylbenzyl ammonium chloride, lauryltrimethyl ammonium bromide, distearylmethylhydroxymethyl chloride, and cetyltrimethyl ammonium chloride.

* * * * *